(12) United States Patent
Xu et al.

(10) Patent No.: US 11,578,140 B2
(45) Date of Patent: Feb. 14, 2023

(54) IMMUNOASSAY FOR MITRAGYNINE

(71) Applicant: MICROGENICS CORPORATION, Fremont, CA (US)

(72) Inventors: Guoping Xu, Milpitas, CA (US); Imad Nashashibi, San Jose, CA (US); Pong Chua, San Jose, CA (US); Chandrasekaran Raman, Sunnyvale, CA (US); Yingqi Lin, Pleasanton, CA (US); Lakshmi Anne, Fremont, CA (US); Anthony Prestigiacomo, Fremont, CA (US)

(73) Assignee: MICROGENICS CORPORATION, Fremont, CA (US)

( * ) Notice: Subject to any disclaimer, the term of this patent is extended or adjusted under 35 U.S.C. 154(b) by 121 days.

(21) Appl. No.: 16/662,408

(22) Filed: Oct. 24, 2019

(65) Prior Publication Data

US 2020/0308306 A1    Oct. 1, 2020

Related U.S. Application Data

(60) Provisional application No. 62/824,184, filed on Mar. 26, 2019.

(51) Int. Cl.
| | | |
|---|---|---|
| *C07D 471/14* | (2006.01) | |
| *G01N 33/94* | (2006.01) | |
| *C07K 16/44* | (2006.01) | |
| *G01N 33/53* | (2006.01) | |

(52) U.S. Cl.
CPC ............ *C07K 16/44* (2013.01); *C07D 471/14* (2013.01); *G01N 33/5308* (2013.01); *C07K 2317/33* (2013.01)

(58) Field of Classification Search
CPC .... C07K 16/44; C07K 16/16; C07K 2317/33; C07K 2317/92; C07D 471/14; A61K 47/646; A61K 47/643; G01N 33/9486; G01N 33/5308
See application file for complete search history.

(56) References Cited

U.S. PATENT DOCUMENTS

| | | |
|---|---|---|
| 4,444,887 A | 4/1984 | Hoffman |
| 4,472,500 A | 9/1984 | Milstein et al. |
| 4,491,632 A | 1/1985 | Wands et al. |
| 4,492,762 A | 1/1985 | Wang et al. |
| 4,593,089 A | 6/1986 | Wang et al. |
| 4,668,640 A | 5/1987 | Wang et al. |
| 4,708,929 A | 11/1987 | Henderson |
| 4,751,190 A | 7/1988 | Chiapetta et al. |
| 4,847,209 A | 7/1989 | Lewis et al. |
| 5,120,653 A | 6/1992 | Henderson |
| 5,571,728 A | 11/1996 | Kraus |

(Continued)

FOREIGN PATENT DOCUMENTS

| | | |
|---|---|---|
| EP | 2769987 A1 | 8/2014 |
| WO | 2013147586 | 10/2013 |

OTHER PUBLICATIONS

Lee Mei Jin. Development of an immunoassay for mitragynine. Ph.D Thesis, University Sains Malaysia, May 2016. pp. 1-24. (Year: 2016).*

(Continued)

*Primary Examiner* — Shafiqul Haq
(74) *Attorney, Agent, or Firm* — Workman Nydegger

(57) ABSTRACT

Compositions, methods, assays, and kits providing or incorporating derivatives of mitragynine, particularly as haptens and immunogens.

8 Claims, 3 Drawing Sheets

(56) References Cited

U.S. PATENT DOCUMENTS

| | | | |
|---|---|---|---|
| 5,604,091 | A | 2/1997 | Henderson |
| 5,643,734 | A | 7/1997 | Henderson |
| 5,798,083 | A | 8/1998 | Massey et al. |
| 5,834,206 | A | 11/1998 | Neuenhofer et al. |
| 6,248,597 | B1 | 6/2001 | Eda et al. |
| 6,448,091 | B1 | 9/2002 | Massey et al. |
| 6,514,770 | B1 | 2/2003 | Sorin |
| 7,138,504 | B2 | 11/2006 | Bodepudi et al. |
| 9,952,206 | B2 | 4/2018 | Benvhikh et al. |
| 2005/0176080 | A1 | 8/2005 | Bodepudi et al. |
| 2010/0209542 | A1 | 8/2010 | Boyer et al. |

OTHER PUBLICATIONS

International Search Report and Written Opinion received for PCT Patent Application No. PCT/US2020/022382, dated Jun. 19, 2020, 12 pages.

Lee et al., "Development of an ELISA for detection of mitragynine and its metabolites in human urine", Analytical Biochemistry, vol. 599, Apr. 14, 2020, p. 113733.

Levy et al., "Radioimmunoassay for reserpine", Life Sciences, Pergamon Press, vol. 19, No. 9, Nov. 1, 1976, pp. 1421-1429.

Supattra et al., "Development of indirect competitive ELISA for quantification of mitragynine in Kratom (Mitragyna speciosa(Roxb.) Korth.)", Forensic Science, vol. 244, Aug. 21, 2014, pp. 70-77.

U.S. Appl. No. 62/824,184, filed Apr. 26, 2019, Guoping Xu.

Kohler et al. Continuous cultures of fused cells secreting antibody of predefined specificity Nature vol. 256, pp. 495-497(1975).

Limsuwanchote et al. Development of indirect competetive ELISA for quantification of mitragynine in Kratom (Mitragyna speciosa (Roxb.) korth) Forensic Science Journal 244 (2014) 70-77.

Methods in Enzymology 73B:3 (981).

Philipp et al "Monitoring of kratom or Krypton intake in Urine using GS-MS in clinical and forensic toxicology" Anal Bioanal Chem (2011) 400:127-135.

\* cited by examiner

Structure I

IMMUNOASSAY FOR MITRAGYNINE

CROSS-REFERENCE TO RELATED APPLICATIONS

This application claims the benefit of and priority to U.S. Provisional Patent Application Ser. No. 62/824,184, filed Mar. 26, 2019, entitled IMMUNOASSAY FOR MITRAGYNINE, the entirety of which is incorporated by reference herein.

BACKGROUND

1. Technical Field

The present disclosure generally relates to compositions, kits, and methods for measuring the concentration of mitragynine in a sample of human biological material, and particularly in a fluid sample, including oral fluid, urine, serum, plasma, or whole blood. In particular, the present disclosure relates to the preparation and use of haptens (immunogen precursors) and immunogens derived from mitragynine and useful for producing antibodies specific for mitragynine and/or metabolites of mitragynine, and to labeled conjugates and immunoassays for measuring the concentration of mitragynine or metabolites of mitragynine, and to methods of manufacturing and using the same.

2. Related Technology

Mitragynine (IUPAC name: methyl (E)-2-[(2S,3S,12bS)-3-ethyl-8-methoxy-1,2,3,4,6,7,12,12b-octahydroindolo[2,3-a]quinolizin-2-yl]-3-methoxyprop-2-enoate) is a predominant corynanthe type indole alkaloid component of the plant species, *Mitragyna speciosa*, commonly referred to as "kratom" or "biak-biak". Although kratom leaves have a tradition of medicinal use in some countries, recreational use and abuse of kratom has led to an increase in mitragynine addiction and fatalities. The recent increase in recreational drug-induced psychostimulation, and the concomitant variety and number of substances ingested to achieve this effect, includes the use of kratom. Kratom is purported to have medicinal properties and, although illegal in certain countries, it remains legal in the UK and in most of Europe and the U.S., although it is classified as a substance of concern by the U.S. Drug Enforcement Agency and banned in some states.

There have been recent reports of numerous fatalities associated with its ingestion and there is increasing interest in kratom detection, by way of mitragynine and other alkaloids of kratom, including but not limited to paynantheine, speciogynine, speciociliatine, 7-hydroxy-mitragine, for toxicological and research purposes. Described analytical methods for detection and quantification of mitragynine and other kratom alkaloids use the relatively expensive, specialist operator-dependent techniques of high performance liquid chromatography (HPLC) or mass-spectroscopy linked to either gas chromatography (GC-MS) or liquid chromatography (LC-MS) (e.g., Kaewklum, 2005; Janchawee, 2007; Le, 2012). The techniques can be further complicated by requiring a sample pre-treatment prior to analysis. Thus, there is a clinical and forensic need to rapidly and economically detect and quantify mitragynine and its metabolites in patient samples and substances suspected of incorporating kratom.

Early methods for detecting and quantifying mitragynine include high performance liquid chromatography (HPLC), and mass spectrometry after separation by gas chromatography (GC-MS) or liquid chromatography (LC-MS).

WO 2013/147586 (Tan et al.) and U.S. Pat. No. 9,952,206 (Benchikh et al.) describe immunoassay methods for detecting and measuring mitragynine and other related alkaloids. Specifically, Tan et al. describes a method of synthesizing mitragynine-p-aminobenzoic acid (PABA-mitragynine) to produce an immunogen used to generate an antibody. Benchikh et al. teach derivatives of 8-desmethylmitragynine (also referred to as 9-hydroxycorynantheidine) for use in production of polyclonal antibodies that bind specifically to mitragynine, 8-desmethylmitragynine, 8-sulphonylmitragynine and/or 8-glucuronidylmitragynine.

Limsuwanchote et al. (*Forensic Science International*, 244:70-77; 2014) teaches a monoclonal antibody (1A6) produced from an immunogenic conjugate of mitragynine acid (16-carboxy mitragynine) and bovine serum albumin. According to Limsuwanchote et al. the carboxylic group was added to mitragynine to permit conjugation to the antigenic protein (to produce an immunogen). The resultant monoclonal antibody was used in an indirect ELISA assay measuring binding to the coating antigen (mitragynine-glutaraldehyde-ovalbumin and showed a significantly higher affinity for the coated antigen-ovalbumin complex than for free mitragynine. Because the ELISA immunoassay was developed for the purpose of quantification of mitragynine in samples extracted from kratom leaves, no human samples were tested. The measurement range of the assay developed by Limsuwanchote et al. was 32.92-250 μg/ml, which is not sufficiently sensitive for testing human samples for the presence of mitragynine.

Randox Laboratories Limited has commercialized an ELISA immunoassay that quantitatively measures mitragynine and 9-O-desmethylmitragynine, with a low level of cross-reactivity to 7-alpha-hydroxymitragynine, from urine and whole blood with a limit of detection of approximately 0.54 ng/ml (in whole blood).

Philipp et al. (*Anal Bioanal Chem*, 400:127-135, 2011) used a GC-MS procedure to screen for mitragynine in urine, which is a common sample for screening for drugs of abuse. Because of the extensive metabolism of kratom alkaloids, Philipp et al. emphasized the need to include metabolites when screening for kratom use, and determined that, in addition to mitragynine, the metabolites 16-carboxy mitragynine (mitragynine acid), 9-O-demethyl mitragynine, and/or 9-O-demethyl-16-carboxy mitragynine are suitable for inclusion in assays for monitoring kratom use.

3. Problems in the Art

At least one antibody specific to a target antigen typically forms the basis of a useful immunoassay, but small molecules such as drugs often are not immunogenic and, therefore, do not elicit an immune response when injected into animals, including those commonly used for commercial antibody production like mice, rats, rabbits, goats, horses and other mammals known in the art. Moreover, some active forms of the target drug may be toxic to the recipient animal, even in small doses. Therefore, a derivative of the target drug may need to be made to serve as the immunogen for antibody generation. However, the antibodies produced in response to the derived target must still be able to cross-react with the drug expected to be present in patient samples.

Accordingly, there are a number of problems in the field of immunoassay generation for small molecules, including immunoassays for mitragynine detection, that can be addressed, particularly when developing antibodies and other reagents.

BRIEF DESCRIPTION OF THE DRAWINGS

Various embodiments of the present disclosure will now be discussed with reference to the appended drawings. It is appreciated that these drawings depict only typical embodiments of the presents disclosure and are therefore not to be considered limiting of its scope.

BRIEF SUMMARY

Figure 1:
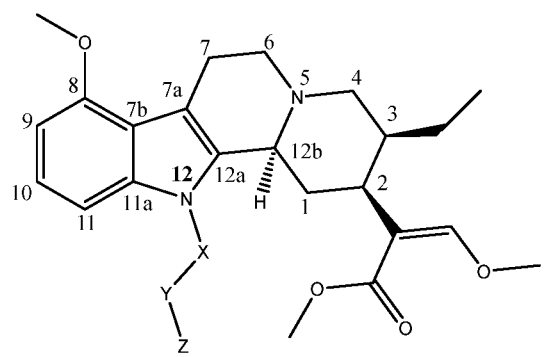
FIG. 1 illustrates a compound having the general structure (I), comprising an immunogens (or hapten-carrier immunogenic complex that comprises a hapten component comprising a derivative of mitragynine) according to an embodiment of the present disclosure.
Figure 2:
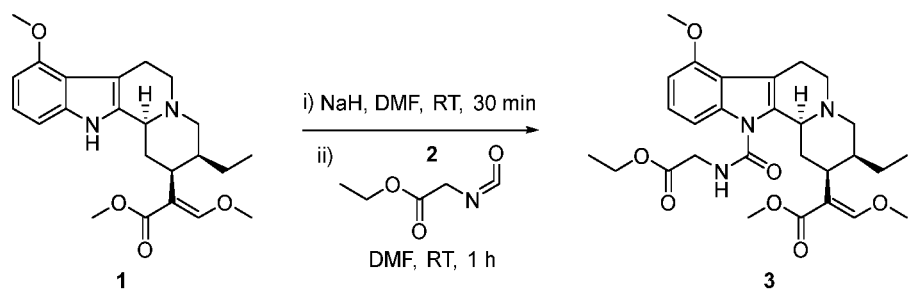
FIG. 2 illustrates production of an Ester (Compound 3) from Compound 1 according to an embodiment of the present disclosure.
Figure 3:
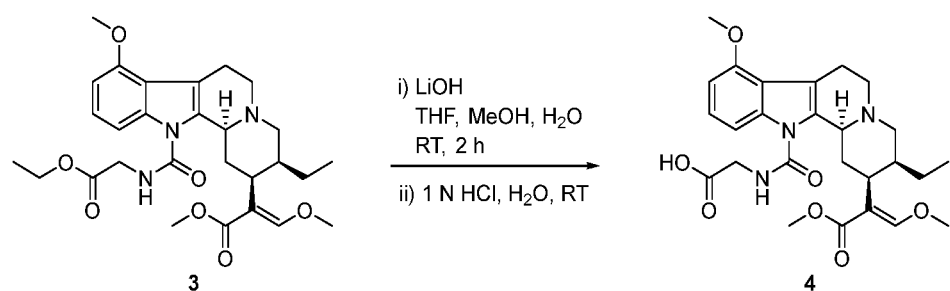
FIG. 3 illustrates production of a Mitragynine (derived) Hapten (Compound 4) from Compound 3 according to another embodiment of the present disclosure.
Figure 4:
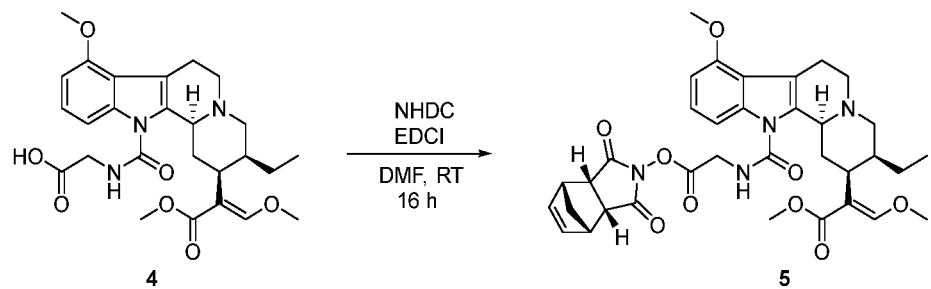
FIG. 4 illustrates production of an activated Ester (Compound 5) of the Mitragynine Hapten (Compound 4) according to another embodiment of the present disclosure.
Figure 5:
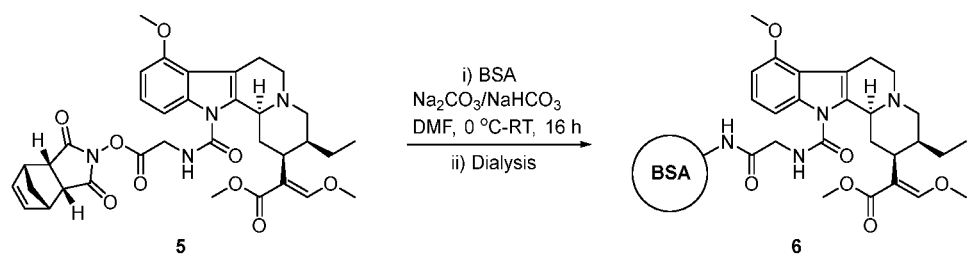
FIG. 5 illustrates production of a Mitragynine (derived) immunogen (Compound 6) from Compound 5 according to another embodiment of the present disclosure.
Figure 6:
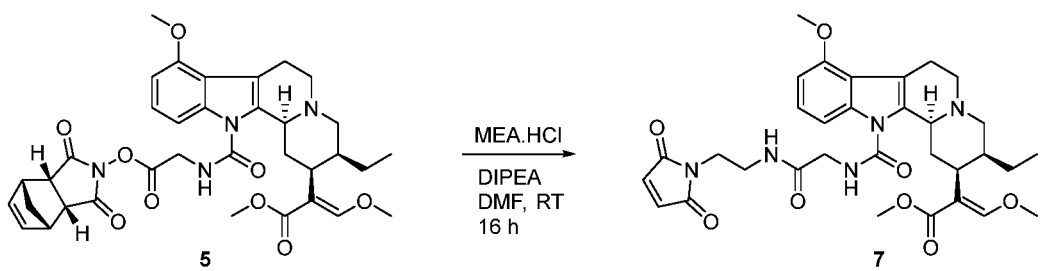
FIG. 6 illustrates production of a Mitragynine MEA Adduct (Compound 7) from Compound 5 according to another embodiment of the present disclosure.
Figure 7:
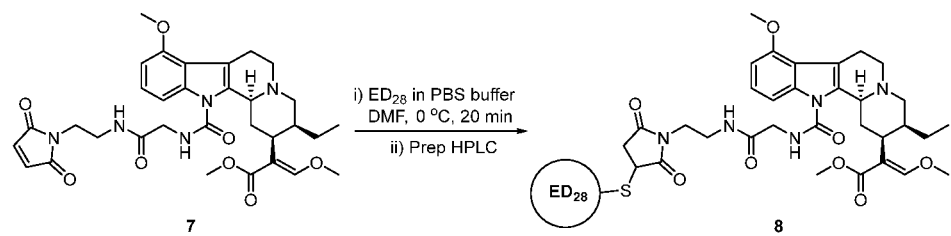
FIG. 7 illustrates production of an enzyme donor conjugate (Compound 8) from Compound 7 according to another embodiment of the present disclosure.
Figure 8:
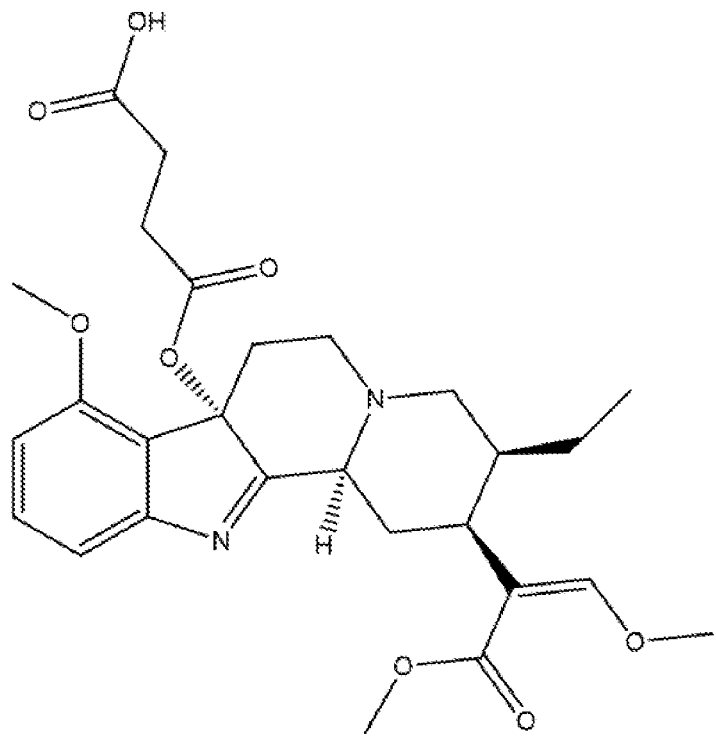
FIG. 8 illustrates an alternative Hapten derived from Mitragynine according to another embodiment of the present disclosure.

The present disclosure relates to the field of drug analytics and the detection and quantification of the main constituent of *Mitragyna speciosa*, commonly referred to as 'Kratom', mitragynine (systematic name: (E)-2-[(2S,3S,12b5)-3-ethyl-8-methoxy-1,2,3,4,6,7,12,12b-octahydroindolo [2,3-a]quinozilizin-2-yl]-3-methoxy propenoic acid methyl ester), with low cross-reactivity, if any, to principle metabolites, including 16-carboxy mitragynine (mitragynine acid) and 9-hydroxycorynantheidine also referred to as 8-desmethyl-mitragynine (systematic name: (E)-2-[(2S,3S,12b5)-3-ethyl-8-hydroxy-1,2,3,4,6,7,12,12b-octahydroindolo [2,3-a]quinozilizin-2-yl]-3-methoxy propenoic acid methyl ester).

The present disclosure solves one or more of the foregoing or other problems in the art with compositions, kits, and methods for detecting mitragynine in a biological sample, such as a bodily fluid. Embodiments can include an immunogenic compound, or immunogen, derived from mitragynine. In some embodiments, the immunogen includes a hapten-carrier complex where the hapten portion consists of a small molecule derived from the structure of mitragynine. The mitragynine-derived hapten (or immunogen precursor) can be conjugated to an antigenic biomolecule (e.g., an antigenic protein, polypeptide, etc.) to create the immunogenic hapten-carrier complex, or immunogen. The immunogen, which is derived from mitragynine and/or includes a mitragynine-derived portion, can be capable of stimulating production of an antibody that (i) interacts specifically with and has a high affinity for at least a portion of the hapten and/or immunogenic hapten-carrier complex and (ii) is specific for or is cross-reactive with at least a portion of the target drug—mitragynine and/or mitragynine metabolite(s). The immunogen, which includes a mitragynine-derived portion, can be operable to trigger a robust immune-response in a suitable animal to which the immunogen is administered and which results in the production of antibodies capable of recognizing, binding, and/or having (strong) affinity and specificity for the immunogen and/or the mitragynine-derived hapten. Preferably, the immunogen is operable to trigger an antibody-mediated immune response that results in the production of antibodies that are specific for and/or cross-react with mitragynine and/or mitragynine metabolite(s).

Embodiments of the present disclosure can additionally relate to compositions, products, and kits that comprise one or more antibodies raised against and/or specific (or having binding specificity) for mitragynine and/or for mitragynine derivatives. The compositions, products, and kits can additionally include mitragynine and/or one or more mitragynine derivatives, including mitragynine haptens and/or mitragynine derivative precursors. As a non-limiting example, the disclosed products or kits can include one or more immunodiagnostic assays for detecting the presence and/or concentration of mitragynine and/or active metabolite(s) thereof.

Embodiments of the present disclosure can include methods for synthesizing mitragynine derivatives and/or immunogens incorporating the same. The disclosed methods can be used to generate one or more elements of the disclosed compositions, products, and kits. Additionally, or alternatively, elements of the disclosed compositions, products, and kits can be used in various methods disclosed herein. For example, one or more immunodiagnostic assays disclosed herein can be used in disclosed methods for detecting the presence or concentration of mitragynine and/or active metabolite(s) thereof. Thus, embodiments of the present disclosure can include methods of detecting the presence or concentration of mitragynine and/or active metabolite(s) thereof, such as in a bodily fluid.

Embodiments of the present disclosure additionally include methods for synthesizing mitragynine derivatives, which can include operative groups such as antigenic moieties that can be used as haptens in an immunogenic hapten-carrier complex to prepare anti-mitragynine antibodies, antigenic moieties that can be used in immunodiagnostic assays for mitragynine, or tracer moieties that can be used in immunodiagnostic assays. In some embodiments, mitragynine derivatives are provided within the disclosed products and/or kits, such as in competitive immunodiagnostic assays, to compete with mitragynine and/or mitragynine metabolites present in a sample for binding to primary, anti-mitragynine antibodies.

In one aspect, the present invention comprises haptens and derivatives produced by derivatization of the nitrogen atom in the 12 position of the fused heterocyclic ring of mitragynine. The haptens produced may be conjugated to: (i) a carrier polypeptide to produce an immunogen for antibody production; and/or (ii) an enzyme, particle, radioisotope, fluorescent molecule, dye, or other directly or indirectly detectable label to produce a labeled conjugate for use as a detection reagent in an immunoassay of mitragynine and/or metabolite(s) of mitragynine. Further, the primary anti-mitragynine antibodies, haptens, or derivatives/analogs of mitragynine and/or the anti-mitragynine antibodies may be attached to a solid support including particles, multi-well plates, chips and the like for use in immunoassays.

One or more immunogens (or hapten component of the hapten-carrier immunogenic complex that comprises a derivative of mitragynine) of the present disclosure has the general structure (I):

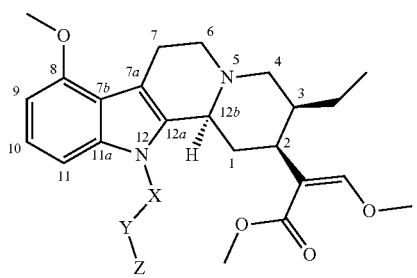

Structure I wherein
X=C, CO, or CS;
Y is an organic spacing group —K-Q-, wherein K=N, O or $C_{(1\text{-}10)}$ comprising a substituted or unsubstituted straight or branched chain, saturated or unsaturated alkylene moiety; and Q=$C_{(1\text{-}10)}$ comprising a carboxylic acid or an ester thereof, an aldehyde, an amino group, a maleimide, a halocarboxylic acid or an ester thereof, a dithiopyridyl moiety, a vinylsulphone moiety, or a thiocarboxylic acid or an ester thereof; and Z is an operative group comprising one or more of detectable labels, antigenic carriers, coupling agents, end groups, proteins, lipoproteins, glycoproteins, polypeptides, polysaccharides, nucleic acids, polynucleotides, teichoic acids, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, or combinations thereof.

In one embodiment, Z is an antigenic carrier comprising one or more proteins, polypeptides, glycoproteins, polysaccharides, particles, microparticles, nucleic acids, polynucleotides, or combinations thereof. In another embodiment, the antigenic carrier is a protein comprising bovine serum albumin ("BSA"), keyhole limpet hemocyanin ("KLH"), egg ovalbumin, bovine gamma-globulin ("BGG"), or combinations thereof.

In another aspect, the invention comprises antibodies produced by inoculation of a mammal with an immunogen. The term "antibody" as used herein refers to polyclonal and monoclonal antibodies and recombinant antibodies, including functional fragments and derivatives thereof. An illustrative method of producing antibodies is to administer the immunogen, generally combined with an adjuvant such as Freund's, in a series of injections to a host animal (e.g., a mammal, such as a mouse, rat, rabbit, etc.) for the purpose of inducing an immunologic response. Such methods are well known to those skilled in the art. Methods for producing monoclonal antibodies were first described by Kohler and Milstein (Nature, Vol 256, pp 495-497, 1975; incorporated herein by reference in its entirety) and have been modified several times since the appearance of that publication. Hybridoma technology has been described in U.S. Pat. Nos. 4,491,632, 4,472,500, and 4,444,887, and Methods in Enzymology, 73B:3 (1981); each is incorporated herein by reference in its entirety. Since the particular method of producing the antibody against the immunogen is not critical, any suitable, acceptable, and/or proven method known in the art can be used to produce a polyclonal or monoclonal antibody using the immunogens described herein.

These and other aspects, features, embodiments, and/or implementations of the present disclosure, and of the invention(s) disclosed and described herein, will become more fully apparent from the following description and appended claims, or may be learned by the practice of the embodiments and/or invention(s) as set forth hereinafter.

This summary is provided to introduce a selection of concepts in a simplified form and that are further described below in the Detailed Description and appended claims, which form a part of the present disclosure. This Summary is not intended to identify key features or essential features of the claimed subject matter, nor is it intended to be used to restrict the scope of the claimed subject matter.

DETAILED DESCRIPTION

Example embodiments are described below. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. In case of a conflict in terminology, the present specification is controlling.

The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference for in their entirety.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the"

include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatuses, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Thus, reference to a specific feature in relation to one implementation should not be construed as being limited to applications only within that implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The word "or" as used herein means any one member of a particular list and also includes any combination of members of that list.

In developing various embodiments of the present disclosure, including immunoassays for the detection of a target drug, such as mitragynine and/or mitragynine metabolites, which lacks inherent immunogenicity, an immunogenic compound, or immunogen, comprising a hapten derived from mitragynine, was made. Briefly, a hapten (derived from the structure of mitragynine) was conjugated to a larger, antigenic protein, polypeptide, or other antigenic biomolecule. The resulting immunogen was capable of stimulating production of an antibody in a mammal that interacts specifically with, and in some instances with high affinity for, at least the hapten portion of the immunogen and not just the hapten-carrier complex comprising the immunogen. The antibody can additionally, or alternatively, be specific and/or cross-reactive with mitragynine or active metabolite(s) thereof.

Further, detection of mitragynine in an immunoassay generally requires the use of a detectable component or label including, but not limited to, radioisotopes, byproducts of an enzymatic reaction (e.g., byproducts of horseradish peroxidase, alkaline phosphatase, glucose oxidase, or beta galacotsidase), fluorescent molecules, and particles. The detectable component can be conjugated to a secondary antibody specific for the primary antibody that is capable of binding mitragynine or an active metabolite(s) thereof.

In embodiments comprising an immunoassay, a target or primary antibody can be conjugated to a reporter (e.g., the detectable component or label) or immobilized to a substrate, as known in the art. The antibody-bound antigen can be detected directly (in the case of a reporter labeled antibody) or detected via a reporter-conjugated secondary antibody. Accordingly, aspects of the disclosure include immunoassays having a primary antibody specific to the target molecule (e.g., mitragynine or active metabolite(s) thereof). Samples potentially containing the target molecule can be assayed, and the presence and/or level of detected signal can be determined therefrom, as known in the art (e.g., an enzymatic reaction product, change in fluorescent signal, etc.).

In some embodiments, a competitive immunoassay is provided. The competitive immunoassay may include a labeled form of the target molecule (e.g., mitragynine or active metabolite(s) thereof) that competes for binding with a limited number of target antibodies. Accordingly, when target molecule is present in a sample, such as one obtained from a diagnostic or drug test detection kit (e.g., for forensic, legal, and/or criminal justice purposes) the target molecule competes with the labeled mitragynine (or active metabolite(s) thereof) for binding to the target antibody, resulting in a detectable (e.g., quantifiable or quantitative) signal. In some embodiments, the detectable signal comprises a difference between the measured amount of detected signal compared to an expected amount of the detected signal. In some embodiments, the detectable signal is an indirect relationship to the concentration of the target molecule in the sample (e.g., less label measured in the competitive immunoassay translates to more of the (unlabeled) target molecule present in the sample.

Optimal immunogens may comprise a drug derivative that includes an antigenic biomolecule and a hapten (derived from the structure of mitragynine) that, in combination, form an immunogen configured to elicit a robust immune-response in a suitable animal capable of producing antibodies against the immunogen and into which the immunogen is introduced. In particular, the structure of an immunogen of the present disclosure acts to trigger a robust immune response that results in the production of antibodies that recognize, bind, and/or have (strong) specificity and/or affinity for the hapten and/or mitragynine and/or metabolite(s) thereof. In certain embodiments, the antibody raised against the hapten-form of mitragynine can have up to 100% cross-reactivity with mitragynine and/or mitragynine metabolite(s). In some embodiments, the antibody can have at least 80%, 85%, 90%, 92%, 95%, 96%, 97%, 98%, or 99% cross-reactivity with mitragynine and/or mitragynine metabolite(s).

The hapten portion of the immunogen (or derivative) and/or the antibody specific to the hapten and/or cross-reactive to mitragynine and/or active mitragynine metabolite(s) can be conjugated to one or more detectable entities, such as labels, markers, enzymes, and so forth, as known in the art. The conjugates can be useful as reagents for developing and performing immunoassays to detect mitragynine and/or mitragynine metabolite(s). Such immunoassays include, for example, enzyme-linked immunoassays (ELISA), fluorescence polarization immunoassays (FPIA), immunoturbidimetric assays, and cloned enzyme-donor immunoassays (CEDIA), among others.

In particular, CEDIA technology has proven to be a highly accurate method for quantitation of therapeutic drugs and drugs of abuse. CEDIA technology is the subject of several patents including U.S. Pat. No. 4,708,929 (incorporated herein by reference in its entirety), which claims competitive homogeneous assay methods, U.S. Pat. No. 5,120,653 (incorporated herein by reference in its entirety) claiming a recombinant DNA sequence for coding the enzyme donor compounds fragment and a host for such a vector, U.S. Pat. No. 5,604,091 (incorporated herein by reference in its entirety), which claims amino acid sequences of the enzyme donor fragment, and U.S. Pat. No. 5,643,734 (incorporated herein by reference in its entirety), which teaches and claims kits for CEDIA™ assays. Competitive homogeneous assays are advantageous over heterogeneous assays, including ELISA assays, because there is no need to separate unbound labeled conjugate from bound labeled-conjugate, which requires time-consuming wash steps.

Further details related to immunogen (or derivative) and/or antibody use and conjugation, detectable entities, such as labels, markers, enzymes, and so forth, and (reagents for) developing and performing immunoassays, including CEDIA assays, can be learned from U.S. Pat. No. 7,138,504 (incorporated herein by reference in its entirety).

Preparation of Haptens, Immunogens, and Detecting Agents

Although haptens provide defined structural epitopes, they are not typically in themselves immunogenic and therefore are often conjugated to carrier materials to generate an immunogen that will elicit an antibody-mediated immune response when administered to a host animal. Appropriate carrier materials commonly contain poly(amino acid) segments and include polypeptides, proteins, and protein fragments. Illustrative examples of useful carrier materials include bovine serum albumin, egg ovalbumin, bovine gamma globulin, bovine thyroglobulin, keyhole limpet haemocyanin etc. Alternatively, synthetic poly(amino acids) having a sufficient number of available amino groups, such as lysine, may be employed, as may other synthetic or natural polymeric materials bearing reactive functional groups. Also, carbohydrates, polysaccharides, or microbial components may be conjugated to the hapten to produce an immunogen. Immunogen formation for the invention described herein involves conventional conjugation chemistry. In order to confirm that adequate conjugation of hapten to carrier material has been achieved prior to immunization, each immunogen can be evaluated using matrix-assisted UV laser desorption/ionization time-of-flight mass spectroscopy (MALDI-TOFMS).

The haptens can also be coupled to a detectable labelling agent to form a conjugate. The detectable labeling agent can be an enzyme (for example, horseradish peroxidase or other enzymes described above), a substance having fluorescent properties or a radioactive label for the preparation of detecting agents for use in the immunoassays. The fluorescent substance may be, for example, a monovalent residue of fluorescein or a derivative thereof.

The process of developing an immunoassay is well known to the person skilled in the art. Briefly, for a competitive immunoassay in which the target is a non-immunogenic molecule such as a hapten, the following process can be conducted: a detecting agent (e.g., a label-conjugated target) is added to a sample containing the target and the target-specific (or cross-reactive) antibodies, and the detecting agent and target compete for binding to the antibodies. The process may comprise fixing the antibodies to a backing substrate, such as a polystyrene solid support or a ceramic chip. The antibodies can be polyclonal or monoclonal obtained using standard techniques. The signal emitted in the immunoassay is proportional to the amount of detecting agent bound to the antibodies which in turn is inversely proportional to the analyte concentration. The signal can be detected or quantified by comparison with a reporter-specific measurement device or calibrator, as known in the art.

Further details related to haptens, immunogens and detecting agents, and to compositions, products, kits, assays, and methods incorporating the same, as well as mitragynine and its metabolites and derivatives, can be learned from U.S. Pat. No. 9,952,206 (incorporated herein by reference in its entirety). Each of U.S. Pub. No. US 2005/0176080 and WIPO Pub. No. WO 2013/147586 are also incorporated herein by reference in its entirety.

EXAMPLES

The following Example further illustrates the invention. It is understood, however, that the Example is set forth by way of illustration and not limitation, and that various modifications may be made by one of ordinary skill in the art.

Example 1: Production of Ester (Compound 3)

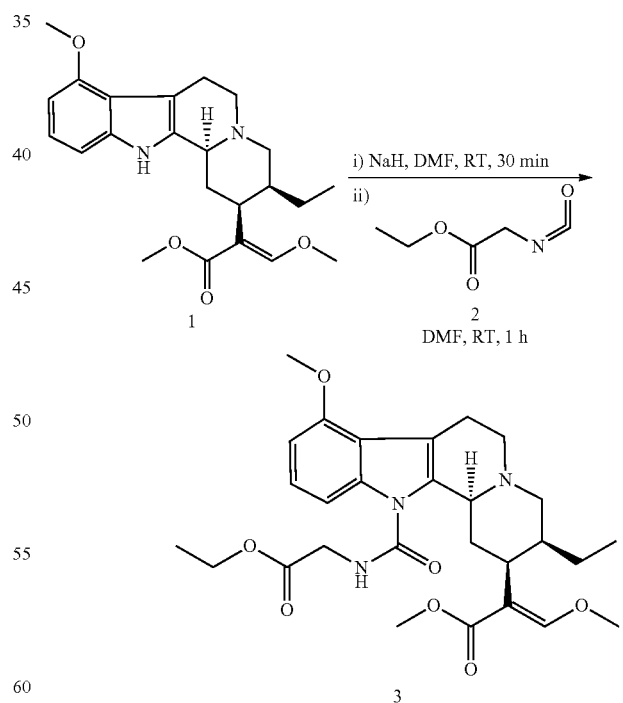

A solution comprising 50.0 mg (0.125 mmol) of mitragynine (Compound 1) in 5.0 ml of dimethylformamide (DMF) at room temperature (RT) was prepared. NaH (60% in oil, 50.0 mg (1.25 mmol) was added with stirring and was stirred at RT for about 25-30 min under nitrogen. Then 162.0 mg (1.25 mmol) ethyl 2-isocyanatoacetate (Compound 2) was added slowly at RT. The resulting mixture was stirred at RT for approximately 2.0 h. HPLC and/or LC-MS analysis showed that more than 95% of the original mitragynine was converted into Compound 3. Dichloromethane (DCM) (25 mL) was added, and the mixture was washed with saturated $NH_4Cl$ (25 mL). Organic layer was separated, dried over $Na_2SO_4$, filtered and concentrated. The crude product was purified by silica gel column chromatography (3% to 5% MeOH in DCM) to give 42.4 mg (~70% purity) of ester (Compound 3) as a light yellow solid.

Example 2: Production of Mitragynine Hapten (Compound 4)

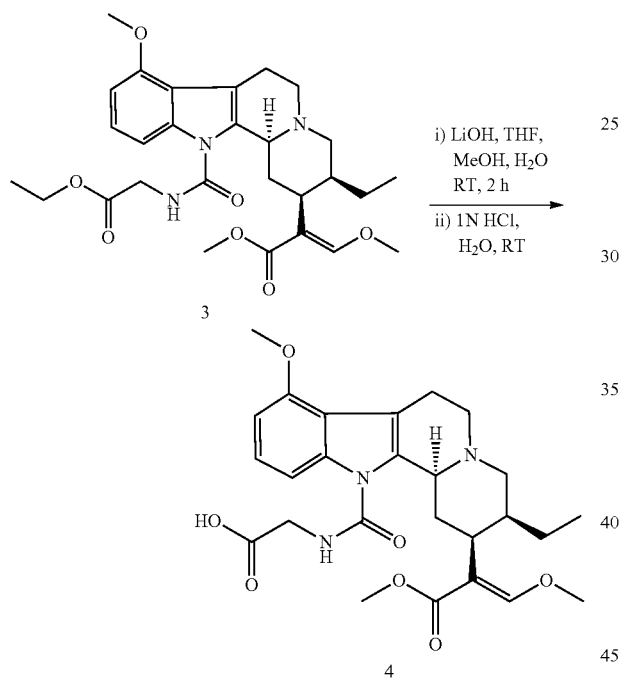

To a solution comprising 42.4 mg (0.054 mmol) of the ester (Compound 3) in 1.0 ml of tetrahydrofuran (THF) and 0.5 ml of methanol at RT, an aqueous solution of LiOH (9.0 mg in 0.5 ml of distilled, 0.21 mmol) was added dropwise at RT. The mixture was stirred at RT for approximately 1.0 h under $N_2$. The conversion of Compound 3 to Compound 4 was monitored by LC-MS. When approximately 100% of Compound 3 was converted to Compound 4, THF and MeOH were removed via rotary evaporator, and the residue was diluted with water (1.5 mL). The aqueous solution was extracted with DCM (2×2.0 mL), cooled to 0° C., acidified with 1N HCl (aq) to pH3. The aqueous mixture was extracted with DCM (3×3.0 mL). The combined organic layers were dried over $Na_2SO_4$, filtered and concentrated to give 25.2 mg (40.4%) of the mitragynine hapten (Compound 4) as a light yellow solid.

Example 3: Production of Activated Ester of Mitragynine Hapten (Compound 5)

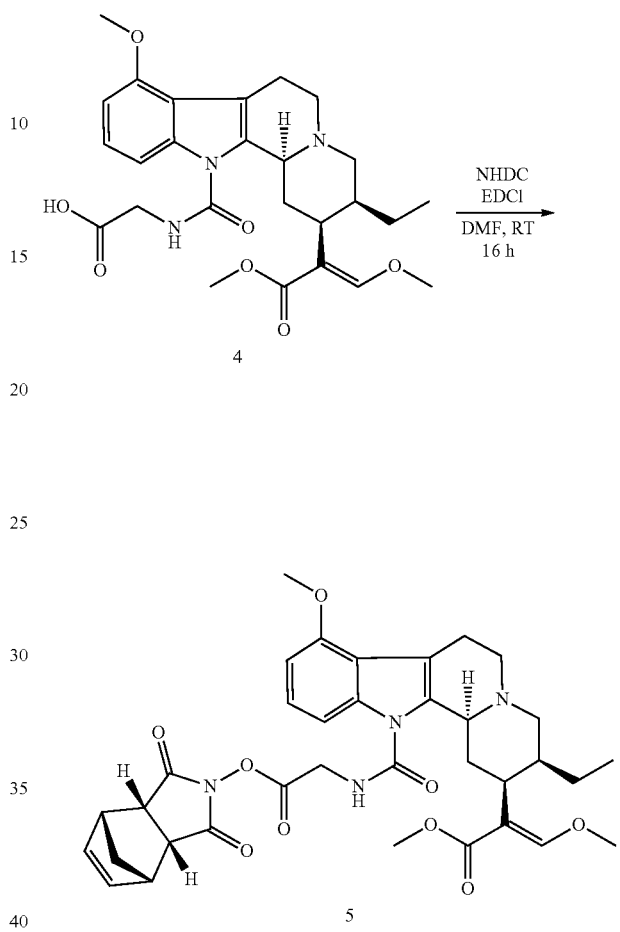

To a stirred solution comprising 9.0 mg (0.018 mmol) mitragynine hapten (Compound 4) in 1.2 ml DMF, was added 8.0 mg (0.045 mmol) of endo-N-Hydroxy-5-norbornene-2,3-dicarboximide (NHDC) and 8.6 mg (0.045 mmol) of 1-ethyl-3-(3-dimethylaminopropyl)carbodiimide (EDCI). The resulting mixture was stirred at RT for approximately 16 h and the crude reaction mixture of activated ester (Compound 5) which was used directly in the next step.

Example 4: Production of Mitragynine Immunogen

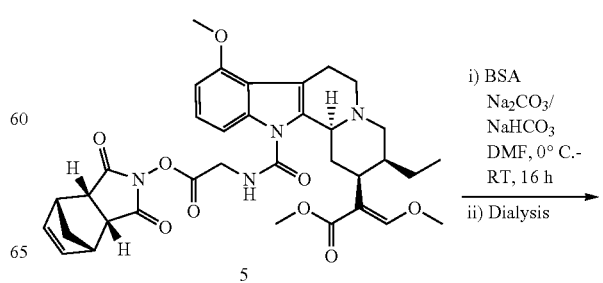

-continued

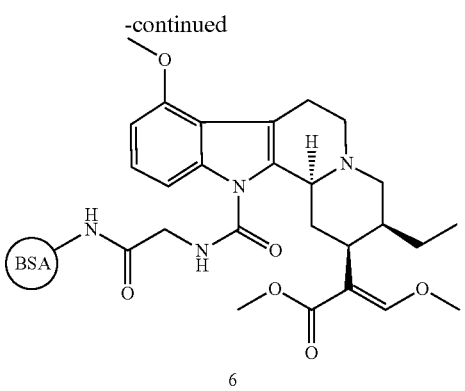

6

Approximately 53.2 mg of BSA was added to approximately 3.0 ml of $Na_2CO_3/NaHCO_3$ buffer (pH=9) with stirring at RT. The resulting clear solution was cooled to about 0° C. for approximately 20 min. A solution of the activated ester (Compound 5) (0.018 mmol in 1.5 ml of DMF was added dropwise at 0° C. and the resulting mixture was stirred at RT for 16 h. The resulting crude immunogen (Compound 6) was purified by dialysis 3 times against phosphate buffer (10 mM $Na_2HPO_4$—$NaH_2PO_4$, pH=7.0). The concentration of mitragynine-BSA immunogen (Compound 6) was measured by using the bicinchoninic acid (BCA) protein concentration assay. The immunogen (Compound 6) had a concentration of 6.0 mg/mL with a hapten number of 9.8 and can be used for the immunizations.

Example 5: Production of Mitragynine MEA Adduct (Compound 7)

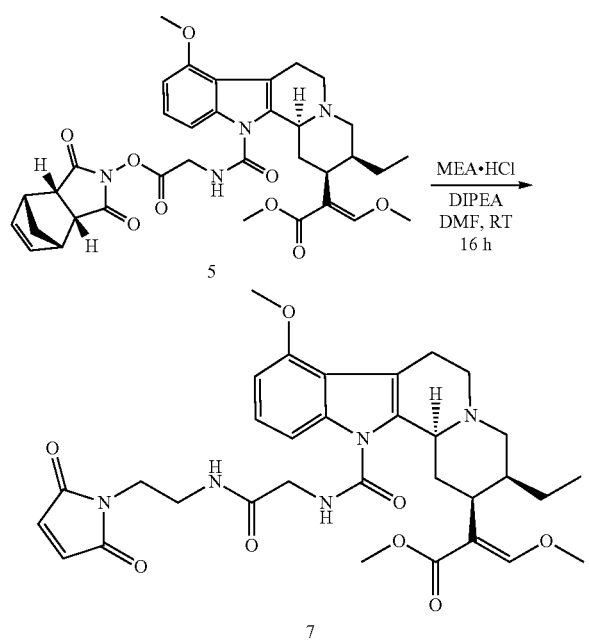

To a stirred solution containing 10.6 mg of the activated ester (Compound 5) in DMF was added 8.4 mg of mercaptoethylamine-HCl (MEA-HCl) and 18.6 mg of diisopropylethylamine. The resulting mixture was stirred overnight (approximately 16 h) at RT. The mixture was directly purified by HPLC to give approximately 5.9 mg of the adduct (Compound 7) as a white solid.

Example 6: Production of Enzyme Donor Conjugate (Compound 8)

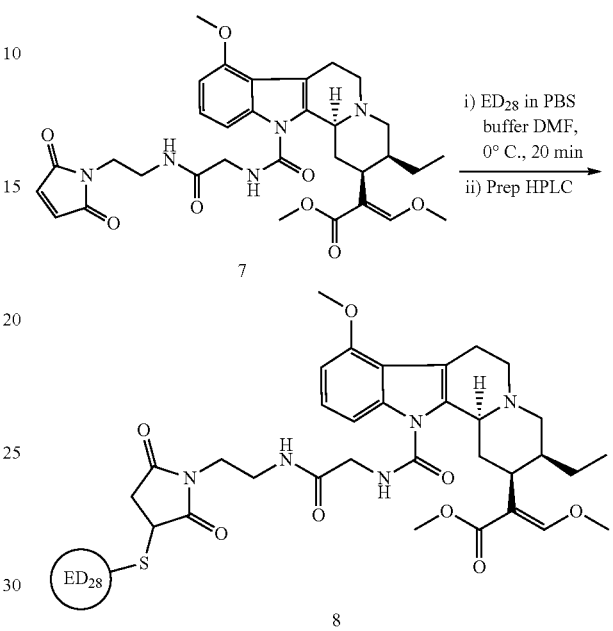

Approximately 0.9 mg MEA adduct (Compound 7) in 0.5 ml DMF was added dropwise to a stirred solution containing 2.0 mg of desalted cloned enzyme donor ED28 in approximately 0.91 ml of phosphate buffer (pH=7.0) at 0° C. The resulting mixture was stirred at 0° C. for approximately 20 min. The crude mixture was purified by HPLC to give approximately 0.63 mg of mitragyinin-ED28 conjugate (Compound 8) in about 10.0 mL mixture of acetonitrile and water with 0.1% TFA as a colorless liquid. The concentration of Compound 8, determined to be about 0.062 mg/ml, was measured using absorbance at 280 nm.

Example 7: Production of Monoclonal Antibodies to Mitragynine and/or Mitragynine Metabolites In a particular embodiment of the invention, the BSA-containing immunogen of Example 4 (Compound 6) was administered to Balb/c mice in a series of injections as is routine in the art. Alternatively, other mammals are suitable for antibody production. Screening of anti-serum samples taken from the immunized mice was performed to assess antibody titer and to evaluate the ability of antibodies in the samples to bind to enzyme-donor conjugate described in Example 6.

Example 8: Development of CEDIA Assay for Mitragynine and/or Mitragynine Metabolites A preferred form of immunoassay is cloned enzyme donor immunoassay or CEDIA assay based upon the re-association of enzymatically inactive polypeptide fragments of β-galactosidase. In particular, β-galactosidase enzyme donor polypeptide fragment combines with a β-galactosidase enzyme acceptor fragment to form active β-galactosidase enzyme.

The active enzyme complex is capable of transforming a substrate into a product that is differentially detectable. Usually, the product is a different color from the substrate and is quantified using spectrophotometric methods. Conjugating a hapten or other small analyte or analyte analog to the enzyme donor fragment at certain sites does not affect the ability to form active enzyme by the complementation reaction and does not affect the rate of enzymatic activity when in the presence of a substrate for β-galactosidase. However, when the enzyme donor-hapten conjugate is bound by the anti-analyte antibody, for example, when little or no analyte is present in a specimen being tested, the complementation reaction is inhibited, reducing the amount of active enzyme present in the reaction mixture. Hence, the enzyme-catalyzed reaction rate is decreased under such conditions. In contrast, when the specimen tested contains significant concentrations of a target analyte, it competes with the enzyme donor-hapten for binding sites on the anti-analyte antibody, thereby increasing the amount of active enzyme formed by complementation reaction. Therefore, the enzyme-catalyzed reaction rate is directly proportional to the concentration of target analyte present in the specimen tested. A preferred β-galactosidase enzyme donor is ED28, a polypeptide containing residues 6-45 of β-galactosidase, with cysteines at positions 1 and 46 (relative to the numbering of the original β-galactosidase fragment).

As an example, CEDIA kits for measuring mitragynine concentrations in biological fluid contain β-galactosidase enzyme acceptor (EA) reagent comprising EA lyophilized in a buffered salt solution, preferably at a concentration of about 0.118 grams of EA per liter of buffered salt solution prior to lyophilization. A preservative such as sodium azide is beneficial to increase the shelf life. Also included is an EA reconstitution buffer that may include an antibody capable of specifically binding mitragynine as described herein. Preferred buffers include PIPES, MOPS, HEPES, TES or Tris.

The enzyme donor (ED) fragment conjugated to mitragynine MEA adduct prepared as described in Example 6 may be supplied in the kit as a separate reagent lyophilized along with the substrate. Chlorophenol-red-β-D-galactopyranoside at a concentration of about 10 nM (about 3.0 g/L) is a preferred substrate. Also, stabilizers, such as bovine serum albumin fragments, and preservatives, such as sodium azide, are beneficial in extending the shelf life. The ED reagent is reconstituted with ED reconstitution buffer comprising potassium phosphate, plus a surfactant, and preservative. Additional components of the kit include instructions for performing the assay. Optionally, the kit may include calibrators, for example, at least one with no mitragynine (0 ng/mL mitrogynine) and one in a higher concentration range (≥200 ng/mL) and controls comprising known concentrations of the drugs. Calibrators and/or controls may be included in kits or provided as separate components.

Example 9: Development of Homogeneous Microparticle Immunoassay

Homogeneous microparticle immunoassay ("HMI") technology, which can be referred to as immunoturbidimetric assays, is based on the agglutination of particles and compounds in solution. Immunoturbidimetric assay technologies are described in U.S. Pat. Nos. 5,571,728, 4,847,209, 6,514,770, and 6,248,597, which are included herein by reference. Briefly, in homogeneous assay methods use is made predominantly of light attenuation, nephelometric, or turbidimetric methods. When particles and/or chemical compounds agglutinate, the turbidity of a solution increases. HMI assays can be configured to be performed with mitragynine and/or a mitragynine hapten (analog) loaded onto a microparticle, or with an anti-mitragynine antibody loaded onto a microparticle. The use of an analog loaded microparticle can be especially advantageous because of the ability to efficiently load the microparticle. In any event, HMI or immunoturbidimetric assays are well known in the art for measuring concentrations of drugs in a sample.

Example 10: Fluorescence Polarization Immunoassay for Mitragynine

Fluorescence polarization immunoassay (FPIA) technology is based upon competitive binding between an antigen/drug in a sample and a known concentration of labeled antigen/drug. FPIA technology is described in U.S. Pat. Nos. 4,593,089, 4,492,762, 4,668,640, and 4,751,190, which are incorporated herein by reference. Accordingly, the FPIA reagents, systems, and equipment described in the incorporated references can be used with anti-mitragynine antibodies.

Example 11: Chemiluminescent Microparticle Immunoassay for Mitragynine

A competitive assay using chemiluminescent microparticle immunoassay ("CMIA") technology can also be used to assess whether or not mitragynine is present in a sample. Various types of CMIA technologies are well known in the art of heterogeneous immunoassays for determining the presence and/or amount of a chemical entity in a sample. Some CMIA technologies can be exemplified by U.S. Pat. Nos. 6,448,091, 5,798,083, and 5,834,206, which are incorporated herein by reference. CMIA assays can include the use of anti-mitragynine antibodies, which are capable of binding to mitragynine and/or its metabolites or analogs, which are coupled to particles, such as magnetic particles or particles suitable for separation by filtration, sedimentation, and/or other means. Additionally, a tracer, which can include a mitragynine analog linked to a suitable chemiluminescent moiety, can be used to compete with free mitragynine in the patient's sample for the limited amount of anti-mitragynine antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RULE). The amount of chemiluminescence is inversely related to the amount of free drug in the patient's sample and concentration is determined by constructing a standard curve using known values of the drug.

The mitragynine haptens, derivatives, analogs, conjugates, antibodies, immunogens and/or other conjugates described herein are also suitable for any of a number of other types of immunoassays with a range of detection systems including but not limited to ELISA assays in multi-well plates, rapid lateral flow assays, and antibody arrays or chips, as well as formats yet to be developed

Example 12: Specificity and Cross-Reactivity

The cross reactivity of the anti-mitragynine antibody derived from the immunogen described above was tested against certain kratom alkaloids and metabolites of mitragynine shown below. The antibody cross-reacts 100% with mitragynine tested at a concentration of 50 ng/ml, and shows only low levels of cross reactivity with the metabolites, 16-carboxy mitragynine (mitragynine acid) and 9-hydroxycorynantheidine. The antibody has ≤0.2% cross-reactivity to the alkaloids 7-OH mitragynine, paynantheine and speciociliatine, tested at higher concentrations as shown in Table 1, below.

TABLE 1

| Compound | Tested Concentration (ng/mL) | Cross Reactivity (%) |
|---|---|---|
| Mitragynine | 50 | 100 |
| 7-hydroxy mitragynine | 35,000-40,000 | ≤0.2 |
| Paynantheine | 25,000-35,000 | ≤0.2 |
| Speciociliatine | 25,000-35,000 | ≤0.2 |
| 16-carboxy mitragynine (Mitragynine acid) | 300-360 | 13.9-16.7 |
| 9-Hydroxycorynantheidine | 3,125-4,000 | 1.25-1.6 |

Example 13: Accuracy of the CEDIA Mitragynine Assay

Using a 50 ng/mL cutoff calibrator, the CEDIA mitragynine assay was compared to liquid chromatography-tandem mass spectrometry (LC-MS/MS) in one hundred human urine samples in qualitative and semi-quantitative modes. The CEDIA assay showed 100% concordance with LC-MS/MS method, as indicated in Table 2, below.

TABLE 2

|  | LC-MS/MS Positive | LC-MS/MS Negative |
|---|---|---|
| CEDIA assay positive | 50 | 0 |
| CEDIA assay negative | 0 | 50 |

Example 14: Precision of the CEDIA Mitragynine Assay

Twenty day precision was performed using a Beckman Coulter AU680 analyzer by testing urine samples spiked with mitragynine, at 25% increments or decrements from the 50 ng/mL cutoff. Samples were tested in replicates of 2 (n=2) twice a day for 20 days (total n=80 for each concentration level), in qualitative and semi-quantitative modes. The precision in qualitative mode was <2% CV and in semi-quantitative mode <10% CV.

Example 15: Alternative Hapten Derived from Mitragynine

The following hapten was also derived from mitragynine.

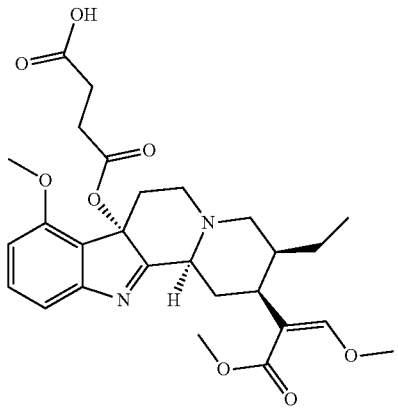 [SMILES: CC[C@@H]1CN2CC[C@@]3(OC(=O)CCC(=O)O)C(=Nc4cccc(OC)c43)[C@@H]2C[C@@H]1/C(=C/OC)C(=O)OC]

CONCLUSION

While the foregoing detailed description makes reference to specific exemplary embodiments, the present disclosure may be embodied or implement in other specific forms without departing from its spirit or essential characteristics. Accordingly, the described embodiments, implementations, aspects, and/or features are to be considered in all respects only as illustrative and/or exemplary, and not restrictive. For instance, various substitutions, alterations, and/or modifications of the inventive features described and/or illustrated herein, and additional applications of the principles described and/or illustrated herein, which would occur to one skilled in the relevant art and having possession of this disclosure, can be made to the described and/or illustrated embodiments without departing from the spirit and scope of the invention as defined by the appended claims.

It will also be appreciated that various features of certain embodiments can be compatible with, combined with, included in, and/or incorporated into other embodiments of the present disclosure. For instance, systems, methods, and/or products according to certain embodiments of the present disclosure may include, incorporate, or otherwise comprise features described in other embodiments disclosed and/or described herein. Thus, disclosure of certain features relative to a specific embodiment of the present disclosure should not be construed as limiting application or inclusion of said features to the specific embodiment. In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein.

The scope of any invention(s) disclosed and/or described herein is indicated by the appended claims rather than by the foregoing description. The limitations recited in the claims are to be interpreted broadly based on the language employed in the claims and not limited to specific examples described in the foregoing detailed description, which examples are to be construed as non-exclusive and non-exhaustive. All changes which come within the meaning and range of equivalency of the claims are to be embraced within their scope.

We claim:

1. A derivative of mitragynine having the general structure:

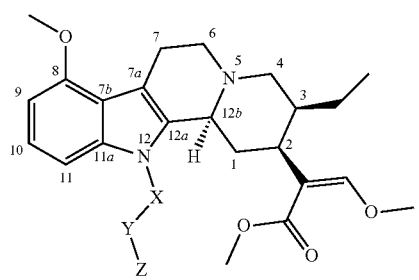

Structure I wherein:
X is CO;
Y is an organic spacing group —K—Y—, wherein K=NH and Q=C$_{(2-4)}$ carboxylic acid or an ester thereof or an amide, wherein X is linked to the organic spacing group —K-Q- at K; and
Z is an operative group selected from the group consisting of coupling agents, lipoproteins, teichoic acids, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, solid supports, liposomes, ligands, receptors, proteins, polypeptides, glycoproteins, polysaccharides, nucleic acids, polynucleotides, and an antigenic carrier selected from the group consisting of bovine serum albumin ("BSA"), keyhole limpet hemocyanin ("KLH"), egg ovalbumin, and bovine gamma-globulin ("BGG").

2. The derivative of claim 1, wherein Z is an antigenic carrier selected from the group consisting of bovine serum albumin, keyhole limpet hemocyanin, egg ovalbumin, and bovine gamma-globulin.

3. The derivative of claim 1, wherein
Q is a C$_{(2-4)}$ carboxylic acid or an ester thereof.

4. The derivative of claim 3, wherein Z is selected from the group consisting of a protein, lipoprotein, glycoprotein, polypeptide, enzyme, enzyme fragment, enzyme donor fragment, enzyme acceptor fragment, enzyme substrate, coenzymes, and an antigenic carrier selected from the group consisting of bovine serum albumin, keyhole limpet hemocyanin, egg ovalbumin, and bovine gamma-globulin.

5. The derivative of claim 1, wherein
Q is an amide.

6. An immunogen precursor derived from mitragynine, the immunogen precursor having the structure:

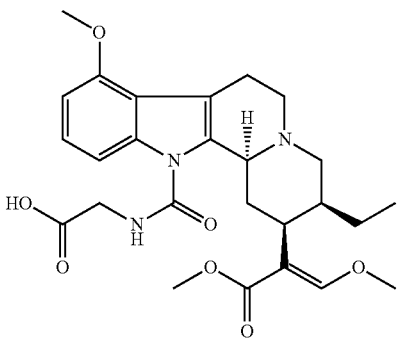

Structure II

7. An immunogen precursor derived from mitragynine, the immunogen precursor having the structure:

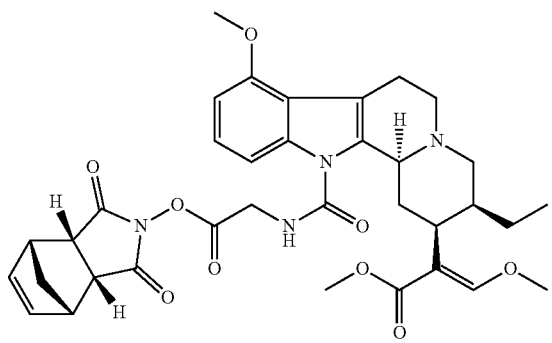

Structure III

8. An immunogen precursor derived from mitragynine, the immunogen precursor having the structure:

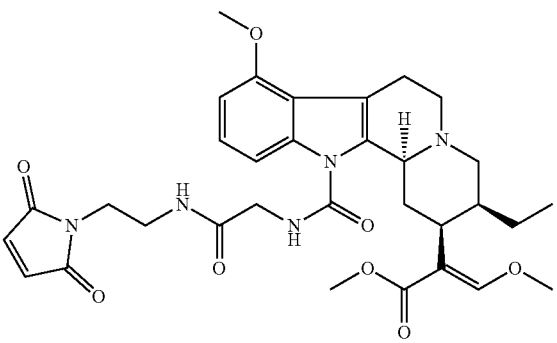

Structure IV

* * * * *